(12) United States Patent
Jordan

(10) Patent No.: US 6,383,136 B1
(45) Date of Patent: May 7, 2002

(54) HEALTH ANALYSIS AND FORECAST OF ABNORMAL CONDITIONS

(76) Inventor: Charlyn Jordan, 14 Schoolhouse Rd., Amherst, NH (US) 03031

(*) Notice: Subject to any disclaimer, the term of this patent is extended or adjusted under 35 U.S.C. 154(b) by 0 days.

(21) Appl. No.: 09/519,491

(22) Filed: Mar. 6, 2000

(51) Int. Cl.$^7$ ............................................... A61B 5/00
(52) U.S. Cl. ............................ 600/300; 128/920; 705/3
(58) Field of Search ................................ 600/300–301; 705/2–3; 128/902–905, 920–925

(56) References Cited

U.S. PATENT DOCUMENTS

| | | | |
|---|---|---|---|
| 5,594,638 A | * | 1/1997 | Iliff ............................ 600/300 |
| 5,956,689 A | | 9/1999 | Everhart, III |
| 6,014,631 A | * | 1/2000 | Teagarden et al. ............. 705/3 |
| 6,151,581 A | | 11/2000 | Kraftson et al. |
| 6,206,829 B1 | * | 3/2001 | Iliff ............................ 600/301 |
| 6,221,011 B1 | | 4/2001 | Bardy |
| 6,270,456 B1 | * | 8/2001 | Iliff ............................ 600/300 |

* cited by examiner

*Primary Examiner*—Kevin Shaver
*Assistant Examiner*—Michael C Astorino
(74) *Attorney, Agent, or Firm*—Fish & Richardson P.C.

(57) ABSTRACT

Tracking the health status of a patient includes entering a plurality of health record signals. Each signal comprises a record of measurement of a predetermined health indicative parameter considered to be in a normal range related to the health status of the patient taken at different times. The health record signals are stored. The stored health record signals are processed to project a possible trend for the predetermined health parameter to assume a value in the abnormal range. A future abnormal indication signal is provided when the trend forecasts the predetermined parameter will assume a value in the abnormal range.

26 Claims, 3 Drawing Sheets

HEALTH ANALYSIS AND FORECAST OF ABNORMAL CONDITIONS

CROSS-REFERENCE TO RELATED APPLICATIONS

Not applicable.

STATEMENT REGARDING FEDERALLY SPONSORED RESEARCH

Not applicable.

The present invention relates to health analysis and forecast of abnormal conditions, and more particularly to a system and method for storing, tracking, and reporting health data, and analyzing a sequence of health data within normal ranges to forecast potential abnormal health conditions of humans and animals.

BACKGROUND OF THE INVENTION

Human and veterinary health practitioners take measurements of various symptomatic indicators in order to detect diseases and various medical conditions in patients. These measurements are typically taken from patients at their visits to their practitioners' offices. Once taken, these measurements are compared to a set of values known to be normal and abnormal for the given indicator at that time to determine whether the patient then has an abnormal condition.

BRIEF SUMMARY OF THE INVENTION

According to the invention, record, track, monitor, and analyze a sequence of health data measurements within a normal range and, in response to the sequence, forecast an abnormal condition. The patient is preferably then treated to avoid development of the abnormal condition. Other features, objects, and advantages of the invention will be apparent from the following detailed description when read in connection with the accompanying drawings in which:

DETAILED DESCRIPTION

Figure 1:
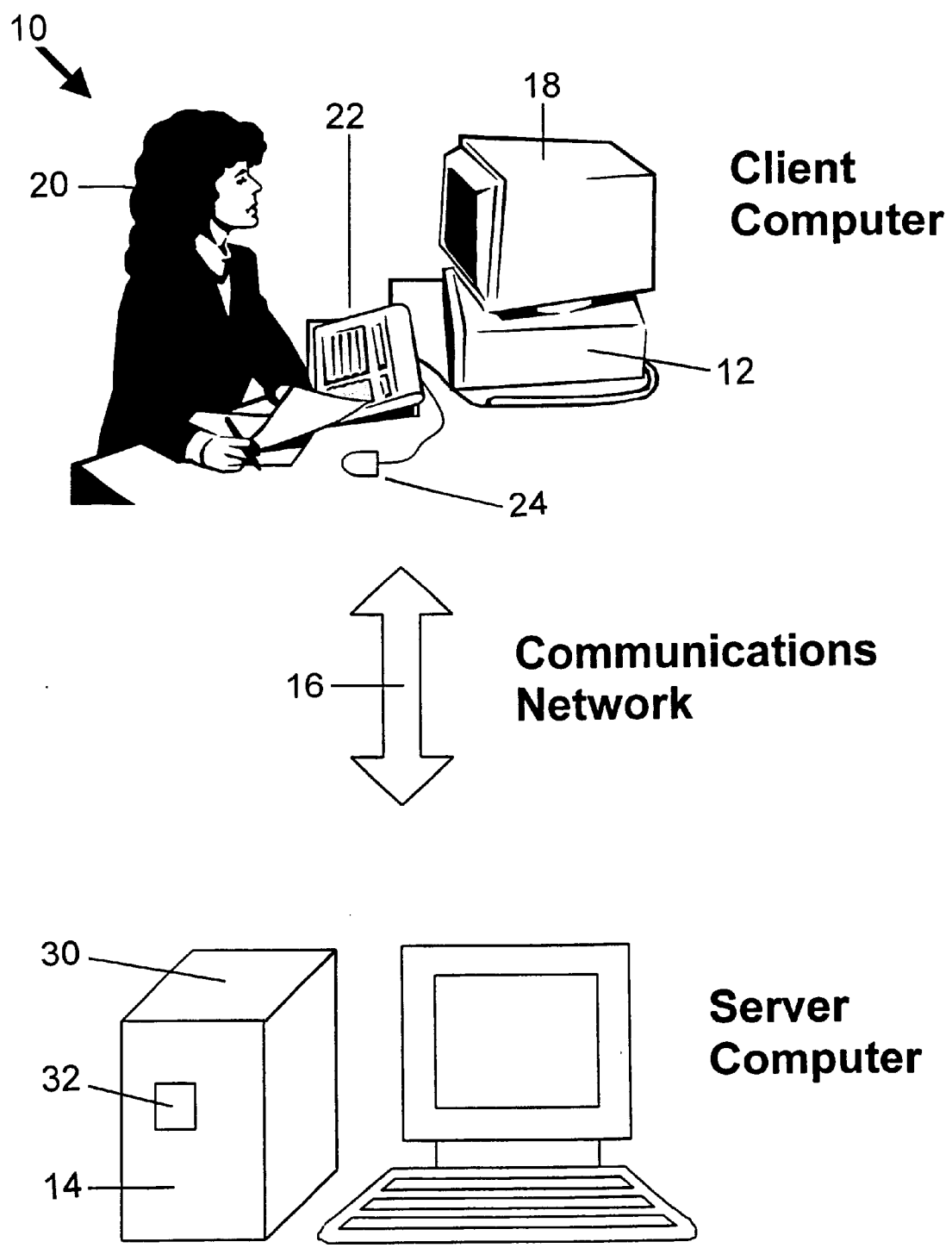
FIG. 1 is a pictorial representation of a system according to the invention.

Referring to FIG. 1, there is shown a pictorial representation of a system according to the invention. System 10 is constructed and arranged to track, analyze and notify users, such as 20, of the health status of patients. System 10 includes an input/output device 12 and a server computer 14. System 10 may be based on internet computer architectures and technologies that provide multiple users, such as 20, worldwide access to system 10 through a number of devices 12 supported by at least one server computer 14. Alternatively, system 10 can be based on intranet or other types of closed system architectures.

Users such as 20, are typically medical professionals, such as doctors, nurses, veterinarians or health technicians, but they may also be any authorized users, including the patient, who have per mission to access system 10. Input/output device 12, here a client computer, serves to connect a user 20 to server computer 14, here a web server computer, through existing communication networks 16. This web server architecture typically may provide a secure link using HTTP protocol and appropriately encrypted signals to ensure confidentiality and accuracy for a patient's health record signals stored within system 10. The architecture also allows users 20 to access system 10 from conceivably any location using, for example, existing phone lines, cable lines, dedicated lines and communication satellites.

Once input/output device 12 links with server computer 14, a user 20 may enter a patient's health record signals into system 10. A patient's health record signals typically comprise records of measurement, or combinations of records of measurements for health indicative parameters for that patient. Health indicative parameters comprise predetermined records of measurement or combinations of records of measurement, that may indicate a trend towards one or more abnormal conditions characterized by one or more parameters being outside a range of normal values, even though all are within a normal range of values. Health record signals are entered into system 10 through input/output device 12, such as with a keyboard 22 and/or mouse 24. Typically, the health record signals are related to records of measurements separated in time by a sequence of time intervals. For example, the patient's health record signals may be taken at routine annual checkups. These health record signals comprise records of measurements typically within a normal range for one or more predetermined health indicative parameters. Health record signals may include, but are not limited to, measurements of parameters such as body fat percentage, electrocardiograms, stress tests, CBC (white blood count, red blood count, hemoglobin, hematocrit, MCV, MCH, MCHC, platelet count), BMP (sodium, potassium, chloride, bicarbonate, anion gap, glucose, BUN, creatinine), LFT (albumin, total and direct bilirubin alkaline phos, ALT/GPT, AST/GOT), HDL-P (cholesterol, triglyceride, HDL-cholesterol, LDL-cholesterol), Monotests, Iron, TIBC, % Sat, FT4, thyroxine, TSH, Total T3, T3 Uptake FTI, Ferritin, Vitamin B12, Folate, DHEA-F, CANCER AG 125-A, Luteinizing Hormone, FSH, Testosterone, Pros Spec Ag, various eye tests such as for Glaucoma, and other parameters.

In other embodiments, patients may have their health record signals input directly into system 10 using other types of input devices, such as keyboards, scanners, microphones, cameras, wireless and mobile devices, other computer systems, and through actual medical sensors and measuring devices. Examples of such medical sensors and measuring devices include, but are not limited to, thermometers, sphygmomanometers, and EKG machines. Data signals may include, but are not limited to, the results of blood tests, urine tests, and other medical tests.

Users 20 can also use input/output device 12 to review previously entered health record signals stored in system 10. Typically, users review such signals through monitors 18 connected to devices 12 linked to server computer 14. In alternative embodiments, device 12, such as a client computer, can be programmed to store and process health record signals offline from server computer 14. In yet other embodiments, stored health records of patients can be output and reviewed by various output devices, including, but are not limited to, printed sheets of paper output by printers (not shown), output by other devices such as facsimile machines, speech synthesizers, other computers, and other devices.

Once entered health record signals are sent to server computer 14 for storage and processing. Server computer 14 typically comprises one or more memory devices, such as 30, and one or more processors, such as 32. Memory device 30 may be one or more hard drives on server computer 14.

Alternatively, memory device 30 may be any storage media, such as, but not limited to, individual file servers, active memory units, tapes, hard disks, optical disks, imaged data, CD-ROM, and other memory and data storage devices.

Memory device 30 may be organized to store health record signals from multiple patients. Memory device 30 organizes all entered health signals of patients in one or more relational databases, indicating patient identities and types of health record signals stored. In other embodiments, additional information can be added or removed from memory 30, such as the identity of the patient's physician, the identify of the patient, known medical history, family history, specific test results, the medical professional treating the patient, and other data.

Processor 32 is preferably one or more dedicated programmable processors, including firmware, hardware, software, located within server computer 14 that analyzes the health record signals stored in memory device 30 as well as forecasts and notifies users of potential abnormal health conditions, despite all the health record signals associated with a specific health condition being within a normal range.

In one example, processor 32 accesses the stored health record signals on the command of a user 20 to project a possible trend for a selected predetermined health indicative parameter. To accomplish this, processor 32 accesses the appropriate health record signals of a patient taken at different times and stored in memory device 30. Processor 32 then uses the set of stored health record signals relating to the predetermined health indicative parameter to project a possible trend toward an abnormal range in the selected predetermined indicative parameter. If processed health record signals indicate a trend towards an abnormal value for the predetermined health indicative parameter, processor 32 returns a future abnormal indication signal for that parameter to user 20. If the trend is not towards an abnormal value, processor 32 may return a no project future abnormality signal.

In another example, processor 32 may be instructed by user 20 to display a patient's stored health record signals of the specified patient. Processor 32 then accesses the appropriate health record signals of the specified patient. In reviewing the patient's stored health record signals, processor 32 may then project the trends for all available predetermined health indicative parameters stored within the system. Again, processor 32 returns any future abnormal indication signals for all health indicative parameters capable of being checked by system 10.

Processor 32 may also be instructed by user 20 to review health record signals for all patients stored in memory 30. Here, processor 32 continuously reviews all health record signals for all patients stored in system 10 and notifies the appropriate user or users when and if it finds a new future abnormal indication signal for a particular patient.

Figure 2:
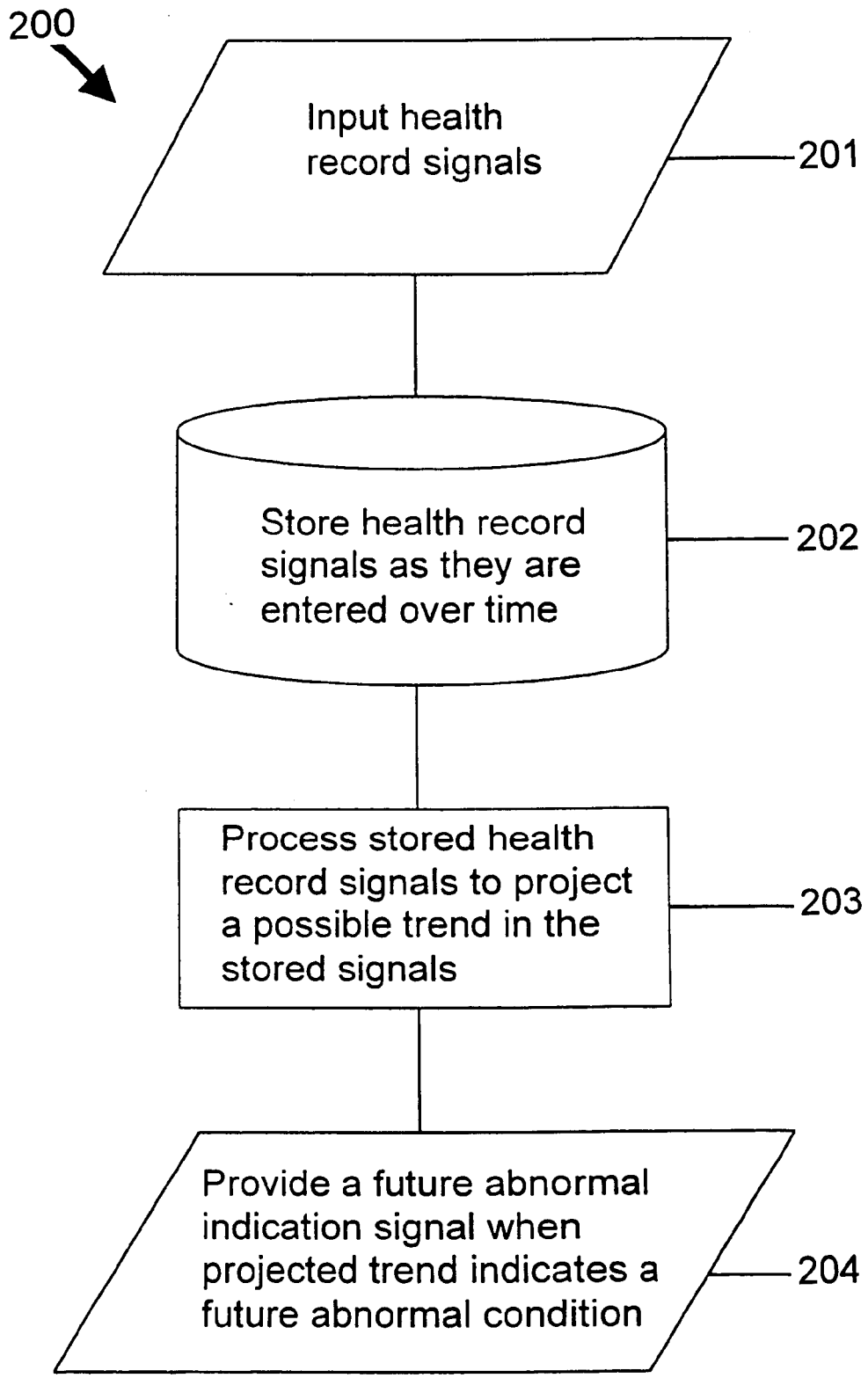
FIG. 2 is a flowchart illustrating the process according to the invention.

Referring to FIG. 2, there is a flow diagram 200 illustrating a method according to the invention. Step 201 shows a user entering a patient's health record signals into the system. The health record signals are typically entered into the system using a keyboard and/or a pointing device, such as a mouse, after they have been measured by a health professional. These health record signals relate to predetermined health indicative parameters that indicate abnormal health conditions when exceeding known thresholds. In an alternative embodiment, the health record signals may be input directly into the system through one or more medical devices that are coupled to a patient.

Step 202 shows the system storing the entered health record signals. The health record signals are stored as they are taken over intervals of time and entered by a user, such as after routine visits to a medical professional. These health record signals, as measured, typically fall within what medical professionals consider normal values for the records when taken. The stored health record signals are used along with other corresponding stored health record signals taken from the patient at other points in time to track and forecast possible future trends in the health indicative parameters to which the health record signal relate.

Step 203 shows the system processing the stored health record signals taken over intervals of time. The stored health record signals are processed to project possible trends for the predetermined health indicative parameter to which the health record signals relate. These possible trends are compared and analyzed against known abnormal ranges for the predetermined health indicative parameters to determine the likelihood that possible projected trends indicate a future abnormal indication in the health indicative parameter. Specific techniques for performing this comparison and analysis will be known to those skilled in the art and are not described in detail to avoid obscuring the invention.

Step 204 shows the system providing a future abnormal indication signal when the analyzed trend indicates a high possibility of an abnormal condition developing in a patient. The future abnormal indication signal forecasts development of a predetermined abnormal health condition before actual development of the abnormal health condition and before its detection by a single measurement of a health record signal in the patient.

Figure 3:
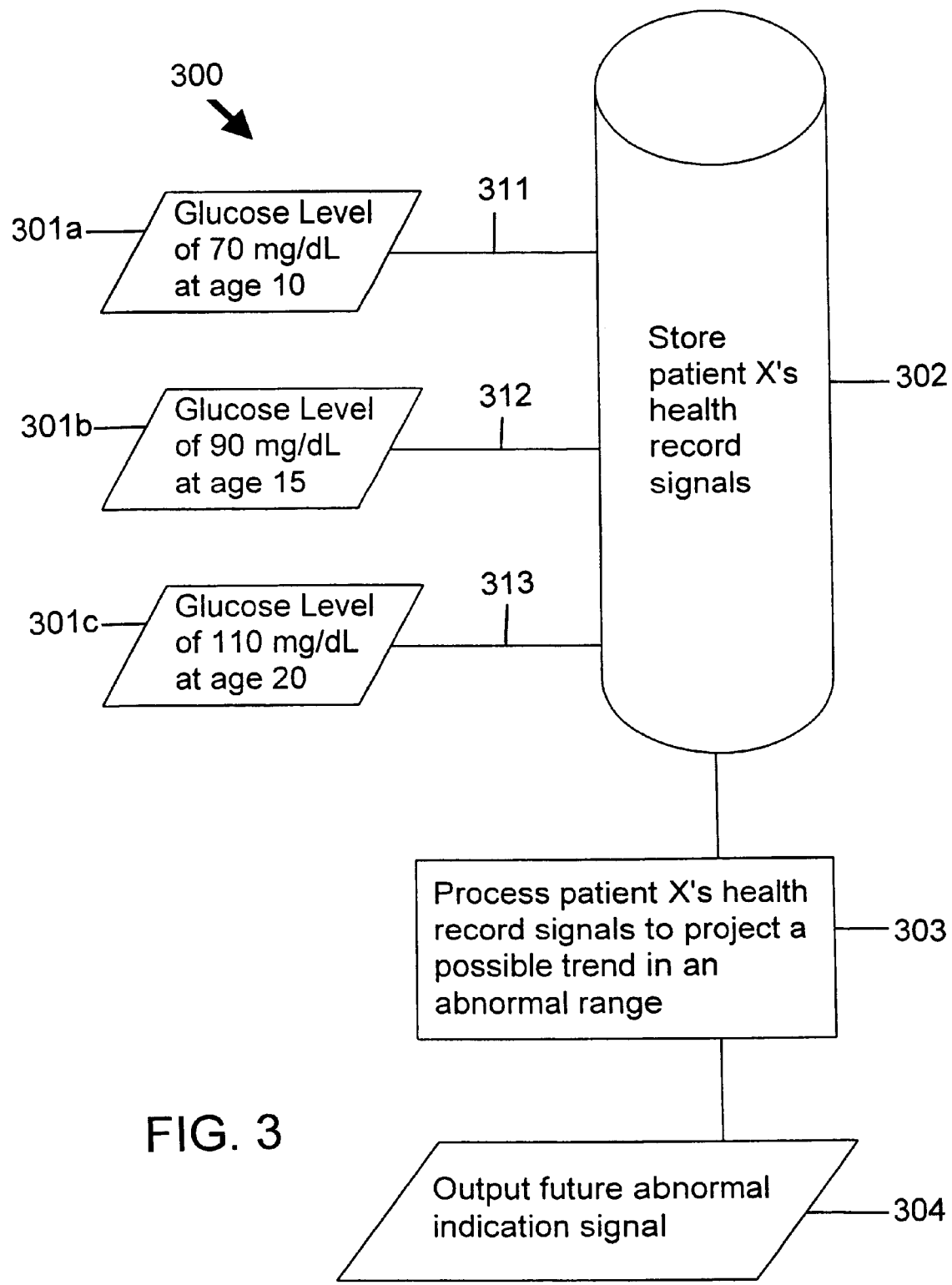
FIG. 3 is a flowchart illustrating an exemplary embodiment of the invention.

FIG. 3 shows a flow diagram 300 depicting an example for tracking, analyzing and forecasting the health status of a male patient X using X's blood FPG (Fasting Plasma Glucose] level as a predetermined health indicative parameter for diabetes. Input block 301a shows X's FPG level of 70 mg/dL at age 10 being input as health record signal 311 into storage block 302. Input block 301b shows X's FPG level of 90 mg/dL at age 15 being input as a health record signal 312 into storage block 302. Input block 301c shows X's FPG level of 110 mg/dL at age 20 being input into storage block 302 as health record signal 313. All three values for X's FPG levels fall within what is considered to be a normal range for X's health indicative parameter for diabetes at those ages. However, process block 303 shows health record signals 311, 312 and 313 being processed to project a possible trend for X's health indicative parameter in an abnormal range. The projected trend indicate a high chance that X's health indicative parameter for diabetes will enter an abnormal, elevated range, that is, FPG levels above 110 mg/dL. Output block 304 shows a future abnormal indication signal being provided to signal that his health record signals indicate that he is likely to be afflicted with diabetes in the next five years. In an alternative embodiment, output block 304 can also provide a course of treatment for X to undertake to prevent, resist, delay, or reduce his chances of developing diabetes, such as by controlling diet with a diabetic diet.

Consider another example of tracking, analyzing, and forecasting the health status of a patient Y using multiple health record signals of TSH and T4, a predetermined health indicative parameter for Y developing hypothyroid condition. Patient Y's TSH levels and T4 levels are input into the system at various points in time. At three two-year intervals in time, Y's TSH levels were 2.5 mIU/mL, 4.7 mIU/mL, and 5.4 mIU/mL, respectively, and T4 levels were 10.2 ug/dL, 6.3 ug/dL, and 4.6 ug/dL respectively. Normal range for TSH is 03 –5.5 mIU/ml, and normal range for T4 is 4.5–11.0 ug/dL. The projected trend indicates a high chance that Y's health indicative parameter for hypothyroidism will enter abnormal ranges within the next two years. Future abnormal indication signals may be provided to indicate that his health record signals indicate that he is likely to be afflicted with hypothyroidism in the next two years. In an alternative embodiment, the invention can also provide a course of treatment for Y to undertake to prevent, resist, delay, or reduce his chances of developing hypothyroidism, such as by increasing iodine intake.

A number of embodiments of the invention have been described. Nevertheless, it will be understood that various modifications may be made without departing from the spirit and scope of the invention. For example, the health record signal in FIG. 3 may be replaced by other health record signals, such as electrocardiogram signals for health indicative parameters relating to heart and tissue conditions.

It is evident that those skilled in the art may now make numerous modifications of and departures from the specific apparatus and techniques disclosed herein without departing from the invention concepts. Consequently, the invention is to be construed as embracing each and every novel feature and novel combination of features present in or possessed by the apparatus and techniques herein disclosed and limited only by the spirit and scope of the appended claims.

What is claimed is:

1. A method of tracking patient health status comprising,
   entering a plurality of health record signals, each comprising a record of measurement of a predetermined health indicative parameter considered to be in a normal range related to the health status of the patient taken at different times;
   storing said health record signals;
   processing the stored health record signals to project a possible trend for said predetermined health indicative parameter to assume a value in an abnormal range; and
   providing a future abnormal indication signal when said trend forecasts said predetermined parameter will assume a value in said abnormal range.

2. The method of claim 1, and further comprising, updating said stored health record signals by inputting a new health record signal for the patient as said new health record signal becomes available.

3. The method of claim 2, wherein updating said stored health record signals continues throughout the life of the patient.

4. The method of claim 1, wherein said predetermined health indicative parameter is a glucose level in the patient.

5. The method of claim 4, wherein said health record signals are updated at least once every five years.

6. The method of claim 1, wherein said predetermined health indicative parameter is a TSH [Thyroid-Stimulating Hormone] level and a T4[Thyroxine] level in the patient, representative of the condition of the thyroid.

7. The method of claim 1, further comprising:
   storing said projected possible trend.

8. The method of claim 1, further comprising:
   storing said future abnormal indication signal.

9. The method of claim 1, further comprising:
   providing an authorized user secure access to the stored health record signals.

10. The method of claim 9, wherein the authorized user is the patient.

11. The method of claim 9, wherein the authorized user is a doctor.

12. The method of claim 9, wherein the authorized user is an agent of the patient.

13. The method of claim 9 wherein the authorized user is provided access through an Internet web site.

14. The method of claim 9, wherein the authorized user inputs said health record signals of the patient.

15. The method of claim 1, further comprising:
   recommending a plan of medical treatment based on said future abnormal indication signal.

16. The method of claim 1, further comprising:
   collecting said stored health record signals and organizing them in a memory device containing a plurality of stored health record signals from a plurality of patients.

17. The method of claim 16, further comprising:
   providing said stored health record signals from said patients to an authorized user.

18. A system for tracking patient health status comprising:
   an input device constructed to receive a plurality of health record signals each comprising a record of a measurement of a predetermined health indicative parameter considered to be in a normal range related to the health status of the patient taken at spaced intervals of time;
   a memory device capable of storing said health record signals; and
   a processor configured to analyze said health record signals by projecting a possible trend in the predetermined health indicative parameter to assume a value in an abnormal range and to provide a future abnormal indication signal when said trend indicates said parameter will assume a value in said abnormal range.

19. The system in claim 18, further comprising:
   an output device constructed to provide an authorized user said health record signals, said projected possible trend and said future abnormal indication signal.

20. The system in claim 19 wherein the processor is further configured to determine a recommended plan of medical treatment based on said future abnormal indication signal.

21. The system in claim 20 wherein said output device provides an authorized user said plan of medical treatment.

22. The system in claim 21 wherein said memory device is further capable of storing said plan of medical treatment.

23. The system in claim 18 wherein said memory device is further capable of storing said projected possible trend of the particular health indicative parameter.

24. The system in claim 18 wherein said memory device is further capable of storing said future abnormal indication signal.

25. The system in claim 18 wherein said input device comprises a keyboard and a pointing device.

26. The system in claim 18 wherein said input device is a medical device coupled to the patient.

* * * * *